(12) United States Patent
Marceau et al.

(10) Patent No.: US 9,157,893 B2
(45) Date of Patent: Oct. 13, 2015

(54) DEVICE FOR THE NONDESTRUCTIVE TEST OF A PART

(75) Inventors: Christian Armand Marceau, Lieusaint (FR); Andre Rouff, Elancourt (FR)

(73) Assignee: SNECMA, Paris (FR)

(*) Notice: Subject to any disclaimer, the term of this patent is extended or adjusted under 35 U.S.C. 154(b) by 942 days.

(21) Appl. No.: 13/381,773

(22) PCT Filed: Jun. 8, 2010

(86) PCT No.: PCT/FR2010/051124
§ 371 (c)(1),
(2), (4) Date: Dec. 30, 2011

(87) PCT Pub. No.: WO2011/001056
PCT Pub. Date: Jan. 6, 2011

(65) Prior Publication Data
US 2012/0098531 A1    Apr. 26, 2012

(30) Foreign Application Priority Data
Jul. 2, 2009   (FR) ...................................... 09 54535

(51) Int. Cl.
*G01N 27/72*   (2006.01)
*G01R 33/12*   (2006.01)
*G01N 27/90*   (2006.01)

(52) U.S. Cl.
CPC ..................... *G01N 27/902* (2013.01)

(58) Field of Classification Search
CPC ................................ E21B 19/20; G01Q 60/54
USPC ............ 324/235, 200, 228, 234, 207.16, 218, 324/219, 220, 237, 239; 73/112.01, 865.8
See application file for complete search history.

(56) References Cited

U.S. PATENT DOCUMENTS

| | | | | |
|---|---|---|---|---|
| 4,139,822 A | * | 2/1979 | Urich et al. | 324/219 |
| 4,553,095 A | * | 11/1985 | Schenk et al. | 324/230 |
| 5,065,635 A | | 11/1991 | Burtner et al. | |
| 5,388,447 A | * | 2/1995 | Fitch et al. | 73/54.14 |
| 6,608,478 B1 | | 8/2003 | Dziech et al. | |
| 6,867,586 B2 | * | 3/2005 | Hatcher et al. | 324/239 |
| 6,952,094 B1 | | 10/2005 | Viertl | |
| 7,305,898 B2 | | 12/2007 | Cabanis et al. | |
| 8,299,785 B2 | * | 10/2012 | Bousquet et al. | 324/220 |

(Continued)

FOREIGN PATENT DOCUMENTS

| | | |
|---|---|---|
| EP | 0 907 077 | 4/1999 |
| EP | 2 040 069 | 3/2009 |

(Continued)

OTHER PUBLICATIONS

International Search Report issued on Oct. 4, 2010 in PCT/FR10/051124 filed on Jun. 8, 2010.

(Continued)

*Primary Examiner* — Huy Q Phan
*Assistant Examiner* — Giovanni Astacio-Oquendo
(74) *Attorney, Agent, or Firm* — Oblon, McClelland, Maier & Neustadt, L.L.P.

(57) ABSTRACT

A device for testing to detect defects at a surface or at shallow depth in a part, for example a blade root for an airplane engine fan. The device includes a probe including a sensor, the probe being hinge-mounted to the end of a handle, a guide presenting a reference surface, and a mechanism adjusting the position of the guide parallel to an axis of the handle.

4 Claims, 2 Drawing Sheets

(56) References Cited

U.S. PATENT DOCUMENTS

Figure 1:
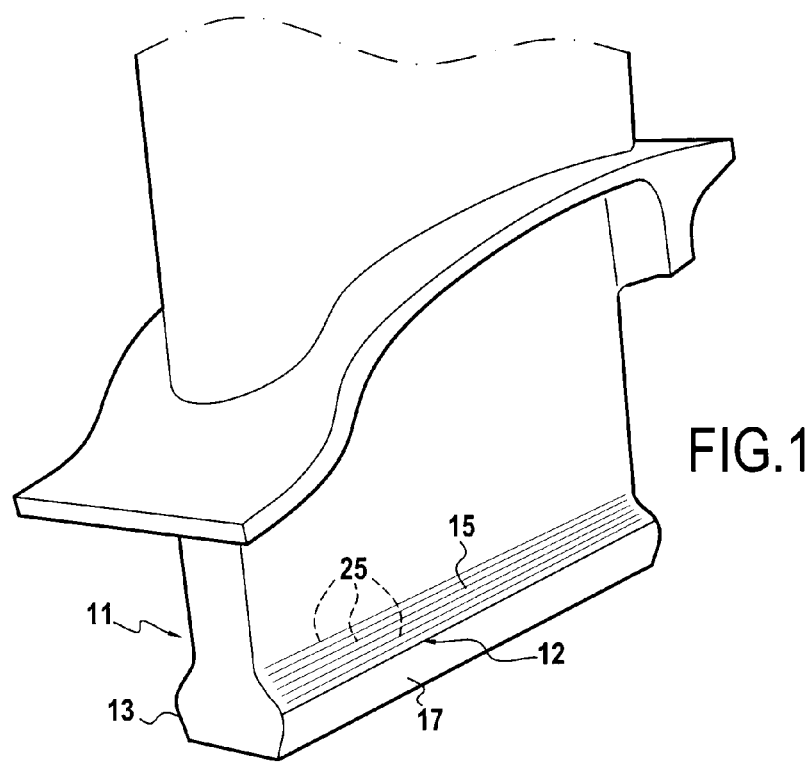

| | | | |
|---|---|---|---|
| 8,499,622 B2* | 8/2013 | Gaisnon et al. | 73/112.01 |
| 2004/0051525 A1 | 3/2004 | Hatcher et al. | |
| 2005/0200355 A1 | 9/2005 | Hatcher et al. | |
| 2005/0204489 A1* | 9/2005 | Velez et al. | 15/21.1 |
| 2006/0091880 A1* | 5/2006 | Feikert et al. | 324/228 |
| 2006/0097719 A1* | 5/2006 | Moore | 324/237 |
| 2007/0044545 A1* | 3/2007 | Beyder et al. | 73/105 |
| 2007/0096728 A1 | 5/2007 | Mader Viertl | |
| 2009/0267598 A1 | 10/2009 | Briffa et al. | |

FOREIGN PATENT DOCUMENTS

| | | |
|---|---|---|
| JP | 11-160286 A | 6/1999 |
| JP | 2006-177941 A | 7/2006 |
| JP | 2007-121300 A | 5/2007 |

OTHER PUBLICATIONS

U.S. Appl. No. 12/211,357, filed Sep. 16, 2008, Briffa, et al.
Office Action issued Jun. 3, 2014, in Japanese Patent Application No. 2012-518109 (with English-language translation).

* cited by examiner

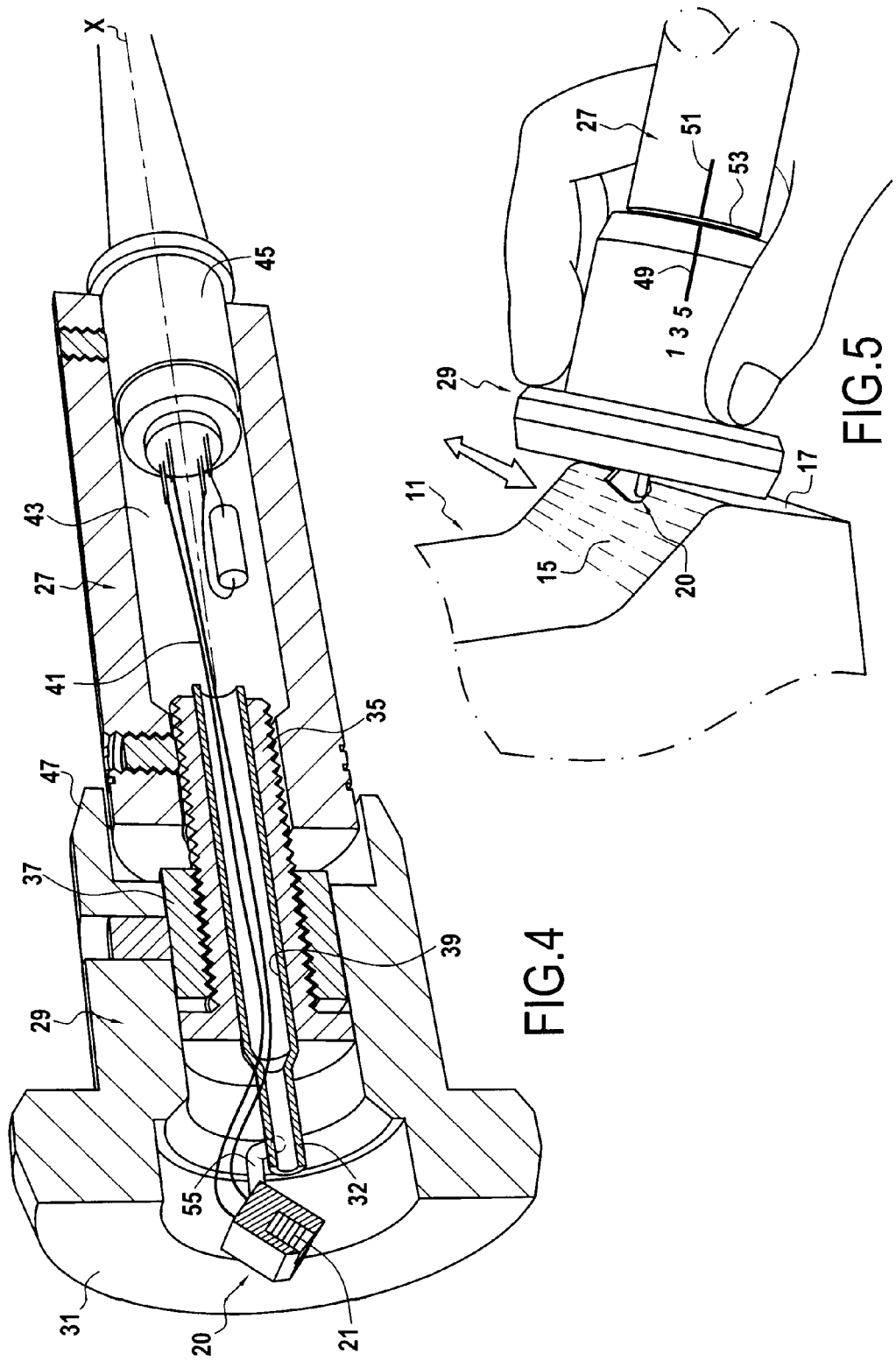

DEVICE FOR THE NONDESTRUCTIVE TEST OF A PART

The invention relates to a device for non-destructive testing of a part, the device operating by moving a sensor over a portion to be scanned. The invention relates in particular to eddy current testing as applied to detecting faults such as cracks (in particular small cracks) existing in or likely to appear in the surface of a part or at a shallow depth therein.

The invention applies most particularly to testing the roots of blades in the fan of an airplane engine.

In a fan under the effect of centrifugal force, blade roots are subjected to high levels of stress, of the order of several tons. The portions the most exposed to fatigue are the contact zones between each blade root and the lateral splines of the slot of the rotor wheel in which the root is installed.

It is known that certain kinds of non-destructive testing are suitable for detecting faults of this type, e.g. ultrasound testing and, above all, eddy current testing.

When performing such non-destructive testing, a probe housing a sensor that develops the phenomenon that is to be used (e.g. a simple coil fed with alternating current for eddy current detection, when the part is made of metal) needs to be moved over the surface of the zone for testing. Moving the sensor over a crack gives rise to a significant disturbance to the signal that is received, which disturbance can be viewed, e.g. on an oscilloscope. In order to ensure that the surface for testing is scanned thoroughly and well, it is necessary to have good control over the path followed by the probe relative to the part. It is accepted that along each path, scanning takes place properly over a strip having a width of a few millimeters. Consequently, in order to scan a certain zone, the best procedure is to describe a plurality of parallel paths that are spaced apart by a given distance that is less than the width of the above-mentioned strip, with said distance being selected to ensure sufficient overlap between the strips.

By way of example, for a blade root of a conventional fan, the generally rectangular surfaces for testing extend over the entire length of the blade root and over a width of about one centimeter. It is therefore necessary to define a plurality of parallel paths that are offset from one another, e.g. six parallel paths extending over the entire length of the blade root. The consequences of a blade breaking are so severe that it is desired to ensure that blade roots are always tested during maintenance operations in order to detect the appearance of the slightest crack that might constitute a break starter.

Until now, testing of this type has required automatic equipment capable of accurately defining the paths, while also guaranteeing that the sensor is accurately orthogonal relative to the surface for testing, throughout the stage in which the surface for testing is being scanned. Such equipment is expensive and cannot be installed in all maintenance units. That is why attempts have been made to develop a manual system that is simple and that presents good performance, suitable for performing this type of testing with good reliability, even in the least well equipped maintenance units.

The invention enables this object to be achieved.

More particularly, the invention provides a device for non-destructive testing of a part by moving a sensor over a portion to be scanned, the device being characterized in that it comprises a probe containing such a sensor, the probe being hinge-mounted at the end of a handle, a guide presenting a reference surface, and means for adjusting the position of said guide in a direction parallel to an axis of said handle.

Thus, the fact of being able to move the guide in controlled manner relative to the probe makes it possible to define different parallel paths by bearing against a common guide surface of the part itself.

As mentioned above, the sensor is advantageously an eddy current sensor, for testing a metal part.

Furthermore, for the specific circumstance of testing a blade root, it is advantageous to take advantage of its constant profile so as to facilitate guidance of the probe and define the various paths.

In other words, the guide and the probe are respectively shaped to come into contact with an inner radial surface of a blade root and with an adjacent outer radial surface of said blade root.

According to an advantageous characteristic, the general shape of the guide is that of a sleeve coaxial with said handle from which said probe emerges.

In order to adapt the position of the probe properly, and in particular in order to ensure that the sensor is always substantially perpendicular to the surface to be scanned, the device is advantageously characterized in that said probe is hinge-mounted to a support in order to be capable of pivoting about an axis perpendicular to the axis of said handle, and in that support is installed in the sleeve at one end of said handle.

According to another advantageous characteristic, the handle includes a threaded segment on which there is mounted a nut that is secured to said sleeve. The threaded segment may be tubular. Advantageously, the inside wall of said tubular threaded segment is lined with a tube projecting into the sleeve and constituting a portion of said support for the probe.

According to another advantageous characteristic, said tube constitutes a duct for passing electric wires, said electric wires being connected to the sensor of said probe.

Figure 2:
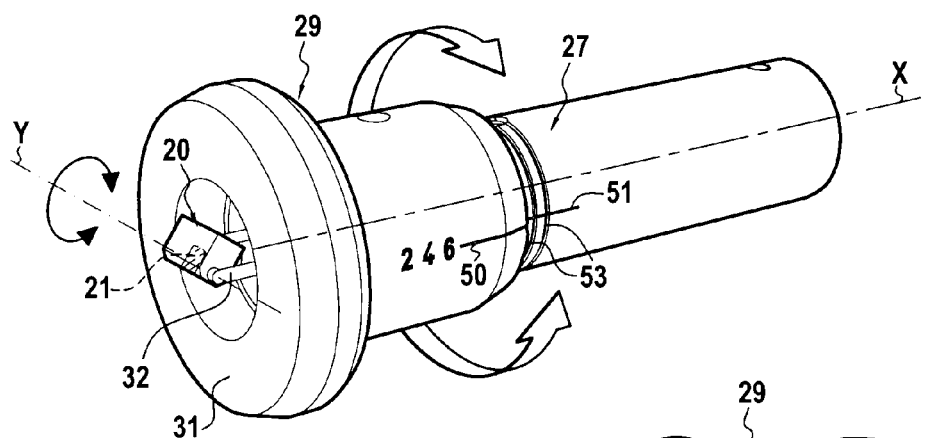
Figure 3:
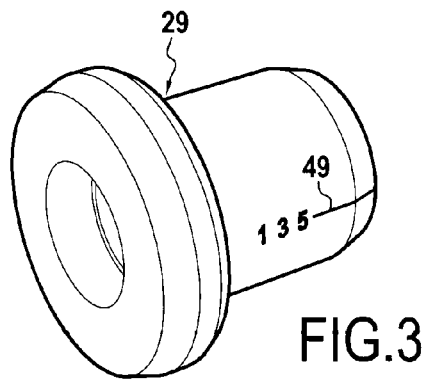

The invention can be better understood and other advantages thereof appear more clearly in the light of the following description of a non-destructive test device in accordance with the principle of the invention, given purely by way of example and made with reference to the accompanying drawings, in which:

FIG. 1 is a perspective view of a blade root to be tested;
FIG. 2 is a perspective view of a test device in accordance with the invention;
FIG. 3 shows the FIG. 2 guide after turning through half a turn;
FIG. 4 is a longitudinal section view of the FIG. 2 device; and
FIG. 5 shows test operations.

On a blade root 11 of the type shown, there can be seen two rectilinear lateral splines 12 and 13 for holding the blade in a slot of the fan wheel. Each spline has an outer radial inclined surface 15 and an inner radial inclined surface 17. The surface 15 is more exposed since, under the effect of centrifugal force, it is in contact with corresponding lateral splines (not shown) of the slot in the rotor wheel. According to an advantageous characteristic, the adjacent surface 17 may serve as a guide surface for manual testing while using a probe of simple design.

The portion for testing is thus in the form of a rectangle of a certain constant width that extends over the entire length of the blade root.

Conventional eddy current testing is performed in this example. It is recalled that a probe containing a coil (sensor) fed with an alternating signal is moved, manually in this example, along a defined path in the zone for testing. The signal generates eddy currents in the metal part, e.g. made of steel or titanium. The signal monitored during the relative movement between the part and the probe is viewed on an oscilloscope in the form of a point of light having a position that is more or less stable so long as the sensor is moving over a surface that is uniform. If the sensor passes over a non-uniformity (an apparent or underlying crack), the point moves suddenly because of sudden variation in the eddy currents in the path. This movement is indicative of the presence of a crack.

It is recalled that in the example described, each path followed by the probe serves to test a narrow strip, and that it has been found that said zone for scanning may be tested effectively by defining six fixed parallel paths that are spaced apart by a predetermined distance, with overlap between the scanned strips serving to guarantee that any crack will be detected.

In order to ensure that testing is effective and reliable, a non-destructive test device has been developed that comprises a probe 20 containing an eddy current sensor 21 that is mounted in hinged manner at the end of a handle 27. Furthermore, the handle is associated with a guide 29 that presents a reference surface 31. More precisely, said guide 29 is generally in the form of a sleeve that is coaxial relative to said handle from which said probe emerges. One end of the sleeve presents an annular front surface constituting said reference surface 31. In the example, this reference surface is defined at the end of an enlarged collar of the sleeve.

The device also includes means for adjusting the position of said guide in a direction parallel to an axis X of said sleeve.

As shown, the probe 20 is mounted on a support 32. More precisely, it is mounted to pivot about an axis Y that is perpendicular to the axis X of said handle. The support 32 is installed in the sleeve at one end of the handle 27. The sleeve forming the guide 29 is movable relative to the handle 27, and consequently relative to the probe 20. For this purpose, the handle includes a threaded segment 35 having mounted thereon a nut that is secured to the guide 29.

The threaded segment 35 is tubular for passing electric wires. Advantageously, the inside wall of the tubular threaded segment is lined with a tube 39 that projects into the sleeve and that constitutes a portion of the support 32 of the probe. The tube constitutes a duct for passing electric wires 41 connected to the sensor 21 of the probe 20. At the other end, the tube 39 opens out into an axial cavity 43 of the handle and the electric wires are connected to terminals of a connector 45 situated at the rear end of the handle 27. After processing, the signal may be displayed on an oscilloscope (not shown).

It can be seen that the sleeve forming the guide 29 has a rear skirt 47 overlapping a cylindrical portion of the handle 27. Consequently, screwing the handle in or out gives rise to an adjustment in the position of the probe 20 relative to the reference surface 31, and this can easily be measured by the movement of the end of the skirt 47 facing the handle. Thus, in order to define the six parallel paths making it possible to scan the entire surface under test, a screw pitch is determined so as to change from one path to another by turning the sleeve through one-half of a turn. Thus, the sleeve carries two diametrically opposite lines 49 and 50. One of the lines 49 corresponds to odd-numbered paths 1, 3, and 5, while the other line 50 corresponds to even-numbered paths 2, 4, and 6. In addition, the handle includes a line 51 and six parallel circular marks 53 corresponding to the six trajectories. In order to go from one trajectory to another, it suffices to turn the sleeve through half a turn, and the rear edge thereof passes from one circular mark to the next.

The narrowed front portion of the tube 39 receives the pivot element of the probe having two opposite branches 55 forming a kind of fork and defining a pivot axis Y about which the probe is constrained to pivot. It has inclined plane facets ensuring that the probe is properly positioned on the surface for testing. In this position, it is certain that the coil 21 constituting the sensor has its axis substantially perpendicular to the surface for testing. When the front surface constituting said reference surface 31 is in contact with the surface 17 of the blade root, then the probe is in contact with the surface 15 of the blade root and with the desired orientation. For each path, testing is preferably performed in two passes starting from the middle of the blade root and going towards one end and then towards the other end.

The invention claimed is:

1. A device for non-destructive testing of a part by moving a sensor over a portion to be scanned, the device comprising:
   a probe including the sensor;
   a handle including a tubular threaded segment, and a support to which the probe is hinge-mounted at a first end thereof; and
   a guide in a form of a sleeve which is coaxial with the handle, a first end of the sleeve surrounding the probe and presenting an annular front face constituting a reference surface; and
   a nut secured at a second end of the sleeve and cooperating with an outer surface of the threaded segment of the handle to adjust a position of the guide in a direction parallel to an axis of the handle,
   wherein the probe is hinge-mounted at the first end of the support and is pivotable about an axis perpendicular to the axis of the handle, and
   wherein an inside wall of the threaded segment is lined with a tube projecting into the sleeve and constituting a portion of the support.

2. The device according to claim 1, wherein the tube constitutes a duct for passing electric wires, the electric wires being connected to the sensor of the probe.

3. The device according to claim 1, wherein the sensor is an eddy current sensor.

4. The device according to claim 1, wherein the guide and the probe are respectively shaped to come into contact with an inner radial surface of a blade root and with an adjacent outer radial surface of the blade root.

\* \* \* \* \*